(12) United States Patent
Zack

(10) Patent No.: US 11,045,373 B2
(45) Date of Patent: Jun. 29, 2021

(54) PERSONAL PORTABLE THERAPY CHAMBER

(71) Applicant: Sunlighten, Inc., Overland Park, KS (US)

(72) Inventor: Aaron Michael Zack, Overland Park, KS (US)

(73) Assignee: Sunlighten, Inc., Overland Park, KS (US)

( * ) Notice: Subject to any disclaimer, the term of this patent is extended or adjusted under 35 U.S.C. 154(b) by 219 days.

(21) Appl. No.: 16/460,590

(22) Filed: Jul. 2, 2019

(65) Prior Publication Data

US 2020/0008996 A1   Jan. 9, 2020

Related U.S. Application Data

(60) Provisional application No. 62/694,619, filed on Jul. 6, 2018.

(51) Int. Cl.
*A61G 10/02*  (2006.01)
*A61N 5/06*   (2006.01)
*A61H 33/02*  (2006.01)

(52) U.S. Cl.
CPC .......... *A61G 10/026* (2013.01); *A61H 33/02* (2013.01); *A61N 5/0616* (2013.01); *A61N 2005/0626* (2013.01); *A61N 2005/0634* (2013.01); *A61N 2005/0638* (2013.01); *A61N 2005/0639* (2013.01); *A61N 2005/0652* (2013.01); *A61N 2005/0659* (2013.01)

(58) Field of Classification Search
CPC .......... A61N 5/0616; A61N 2005/0639; A61H 33/06
See application file for complete search history.

(56) References Cited

U.S. PATENT DOCUMENTS

| | | |
|---|---|---|
| 2,240,819 A | 5/1941 | Waly |
| 3,409,915 A | 11/1968 | Jauvais |
| 3,741,218 A | 6/1973 | Novak |
| 3,754,551 A | 8/1973 | Nielsen |

(Continued)

FOREIGN PATENT DOCUMENTS

| | | | |
|---|---|---|---|
| CN | 107951651 A | 4/2018 | |
| EP | 1810713 A2 * | 7/2007 | ........... A61N 5/0614 |

(Continued)

*Primary Examiner* — Gary Jackson
*Assistant Examiner* — Zahed Kabir
(74) *Attorney, Agent, or Firm* — Erickson Kernell IP, LLC; Kent R. Erickson

(57) ABSTRACT

A portable, personal therapy chamber for provision of infrared radiation therapy. The therapy chamber includes a pair of telescopically positionable cabins that are lightweight and easily portable by a single user. The therapy chamber is configured for use by a single person lying generally prone on a surface. The cabins are disposed to overlie the user and include a plurality of infrared radiation elements that direct infrared energy toward the user's body. When using the therapy chamber, the user's head extends from an open end of the cabin. A facial treatment fixture is integrated with the cabin to be extendable longitudinally from a terminal end thereof and to overlie the user's face/head. The therapy chamber can be configured to provide mild hyperbaric oxygen therapy in addition to infrared therapy.

17 Claims, 8 Drawing Sheets

(56) References Cited

U.S. PATENT DOCUMENTS

| | | | |
|---|---|---|---|
| 3,902,488 | A | 9/1975 | Sheppard |
| 4,003,371 | A | 1/1977 | Fischer |
| 4,044,772 | A | 8/1977 | Schloss |
| 4,623,796 | A * | 11/1986 | Kratz ................... A61N 5/0614 250/454.11 |
| 5,086,769 | A * | 2/1992 | Vianello ................ A47C 1/14 297/395 |
| 5,649,972 | A | 7/1997 | Hochstein |
| 6,255,786 | B1 | 7/2001 | Yen |
| 6,272,697 | B1 | 8/2001 | Park |
| 6,317,636 | B1 | 11/2001 | Fujii |
| 6,489,614 | B1 | 12/2002 | Deguchi et al. |
| 6,497,231 | B1 | 12/2002 | White |
| 6,497,717 | B1 | 12/2002 | Daffer et al. |
| 6,549,809 | B2 | 4/2003 | Ono |
| 6,613,071 | B1 | 9/2003 | Fujii |
| 6,615,419 | B1 | 9/2003 | Chang |
| 6,719,780 | B1 | 4/2004 | Salmon et al. |
| 6,896,693 | B2 | 5/2005 | Sullivan |
| 7,108,712 | B2 | 9/2006 | Barghelame |
| 7,135,035 | B1 | 11/2006 | Dimmick |
| 7,201,766 | B2 | 4/2007 | Butler |
| 7,503,926 | B2 | 3/2009 | Daffer et al. |
| 7,517,101 | B2 | 4/2009 | Tobin |
| 7,575,549 | B2 | 8/2009 | Miller |
| 7,887,533 | B2 | 2/2011 | Barolet et al. |
| 8,057,525 | B2 | 11/2011 | Suzuki |
| 8,084,715 | B2 | 12/2011 | Hall |
| 8,425,577 | B2 | 4/2013 | Vargas et al. |
| 8,447,415 | B2 | 5/2013 | Hirata |
| 8,602,398 | B2 | 12/2013 | Hayasi et al. |
| 8,692,168 | B2 | 4/2014 | Benda et al. |
| 9,533,170 | B2 | 1/2017 | Dye et al. |
| 9,649,252 | B2 | 5/2017 | Kim |
| 9,808,644 | B2 | 11/2017 | Daffer |
| 2002/0183814 | A1 | 12/2002 | Ono |
| 2003/0155535 | A1 * | 8/2003 | Laudano ................ H01J 61/33 250/504 R |
| 2004/0088028 | A1 | 5/2004 | Cameron et al. |
| 2004/0188415 | A1 | 9/2004 | Lee |
| 2004/0260364 | A1 | 12/2004 | Daffer et al. |
| 2005/0050903 | A1 | 3/2005 | Manteiga et al. |
| 2005/0137656 | A1 | 6/2005 | Malak |
| 2005/0256554 | A1 | 11/2005 | Malak |
| 2007/0033069 | A1 | 2/2007 | Rao et al. |
| 2007/0050903 | A1 | 3/2007 | Sappenfield et al. |
| 2007/0110411 | A1 | 5/2007 | Bergstein |
| 2007/0206364 | A1 | 9/2007 | Swei et al. |
| 2007/0294818 | A1 | 12/2007 | Tei et al. |
| 2008/0036383 | A1 | 2/2008 | Lin |
| 2009/0005839 | A1 | 1/2009 | Griffith et al. |
| 2009/0254153 | A1 | 10/2009 | Chang et al. |
| 2010/0017953 | A1 | 1/2010 | O'Keeffe et al. |
| 2010/0063487 | A1 | 3/2010 | Van Straalen |
| 2012/0233765 | A1 | 9/2012 | Altman et al. |
| 2013/0097773 | A1 | 4/2013 | Pinkus et al. |
| 2015/0174003 | A2 | 6/2015 | O'Keeffe et al. |

FOREIGN PATENT DOCUMENTS

| | | | |
|---|---|---|---|
| EP | 1839704 A1 * | 10/2007 | ........... A61N 5/0614 |
| WO | 2007112939 A2 | 10/2007 | |
| WO | 2007117234 A1 | 10/2007 | |
| WO | WO-2014030857 A1 * | 2/2014 | ........... A61N 5/0616 |

* cited by examiner

PERSONAL PORTABLE THERAPY CHAMBER

CROSS-REFERENCE TO RELATED APPLICATIONS

This application claims the benefit of U.S. Provisional Patent Application No. 62/694,619 filed Jul. 6, 2018, the disclosure of which is hereby incorporated herein in its entirety by reference.

BACKGROUND

It has been found that exposure of the human body to near-infrared radiation may provide health benefits, such as increased blood circulation, reduced inflammation, increased healing rates, and/or pain relief, among other benefits. Near-infrared treatment may also be employed to activate photo-reactive medications or substances that are ingested, injected, applied topically, or otherwise provided to a user's body.

Devices, such as dry saunas are known in the art for provision of infrared radiation to a user, but such devices generally limit or eliminate near-infrared radiation in the provided treatment spectrum. Known devices configured to provide near-infrared radiation treatments are large, very expensive beds or chambers that are relatively inaccessible to the common consumer due to cost and/or space requirements. Other devices include small handheld wands that can only treat very small portions of the user's body at any given time. What is needed is a simple near-infrared treatment chamber that can provide treatment to a large portion of a user's body and that is portable, storable, and easily accessible by a user.

Oxygen therapy provided alone or in addition to infrared radiation therapies has also been found to provide beneficial health and wellness effects. However, known devices configured to provide oxygen therapies are massive, complex capsules that are not conducive to in-home use. A simple and easily storable chamber that can provide oxygen therapy alone or in addition to near-infrared radiation therapy would also be a beneficial advance in the art.

SUMMARY

Exemplary embodiments are defined by the claims below, not this summary. A high-level overview of various aspects thereof is provided here to introduce a selection of concepts that are further described in the Detailed-Description section below. This summary is not intended to identify key features or essential features of the claimed subject matter, nor is it intended to be used in isolation to determine the scope of the claimed subject matter. In brief, this disclosure describes a personal and portable therapy chamber.

The personal therapy chamber includes an upper and lower cabin each having a half-cylindrical form. The lower cabin is sized with a radius that is just smaller than that of the upper cabin such that the lower cabin can be moved relative to the upper cabin in a telescoping manner. The cabins are configured to overlie a user that is lying in a generally prone position on a surface with the head of the user extending beyond a terminal end of the upper cabin and the remainder of the user's body being enclosed between the cabins and the surface. A pad or mat may also be provided that can be placed on the surface beneath the user and the cabins.

A plurality of near-infrared emitting elements, such as LEDs are disposed in the walls of the upper and lower cabin to emit near-infrared radiation that is directed toward the user's body. The pad may also be configured to include one or more near-infrared emitting elements.

The upper cabin may include a facial treatment unit that is extendable from a terminal end of the upper cabin. The facial treatment unit may include one or more panels or sections in which near-infrared emitting elements may be disposed and configured to emit near-infrared radiation toward the face of the user.

In another embodiment, a chamber is provided in which a user can be positioned to receive oxygen therapy in addition to near-infrared therapy. An oxygen supply apparatus is operatively coupled with the chamber to provide a supply of oxygen into the chamber to expose the user to a hyper-oxygenated environment for oxygen therapy treatment. A plurality of near-infrared emitting panels are disposed on an interior surface of the chamber and directed toward the user's body. The chamber can be configured in an upright or horizontal orientation to allow the user to be seated or to lie prone in the chamber during the treatment.

The personal therapy chamber includes a control unit through which the user may control the near-infrared elements independently or in groups. The control unit may also be employed to control the facial treatment unit and the oxygen-treatment system.

In one embodiment, a personal therapy chamber that includes a cabin and a plurality of infrared radiation emitting elements is described. The cabin is manually disposable by hand on a surface to define an interior space between a wall of the cabin and the surface in which a single user can be positioned with a head of the user extending at least partially from a terminal end of the cabin. The plurality of infrared radiation emitting elements comprise arrays of infrared-emitting LEDs. The elements are disposed in or on the wall of the cabin and directed toward the interior space to provide infrared radiation to the user positioned within the cabin.

In another embodiment, a personal therapy chamber that includes a cabin, a infrared radiation emitting element, and a facial treatment fixture is described. The cabin is manually disposable by hand on a surface to define an interior space between an interior wall of the cabin and the surface. The cabin includes an upper portion and a lower portion that are telescopically movable relative to one another and is sized to receive a single user within the interior space with a head of the user extending at least partially beyond a terminal end of the upper portion of the cabin. The infrared radiation emitting element comprises an array of infrared-emitting LEDs and is disposed on or in the interior wall of the cabin. The element is directed toward the space to provide infrared radiation to the user positioned within the cabin. The facial treatment fixture includes a second infrared radiation emitting element that comprises a second array of infrared-emitting LEDs and is disposed to extend from a terminal end of the upper portion of the cabin.

In another embodiment, a personal therapy chamber that includes a cabin, a near-infrared radiation emitting element, a pressurization system, and a control unit is described. The cabin enclosure is sized to receive a single human user therein. The near-infrared radiation emitting element is disposed on an interior wall of the cabin and is configured to direct near-infrared radiation toward the user. The pressurization system is communicably coupled to an interior of the cabin and is adapted to increase a barometric pressure within the cabin to a level greater than 1.0 atmosphere. The control unit is adapted to control operation of the near-infrared radiation emitting element and the pressurization system.

DESCRIPTION OF THE DRAWINGS

Illustrative embodiments are described in detail below with reference to the attached drawing figures, and wherein.

DETAILED DESCRIPTION

Figure 1:
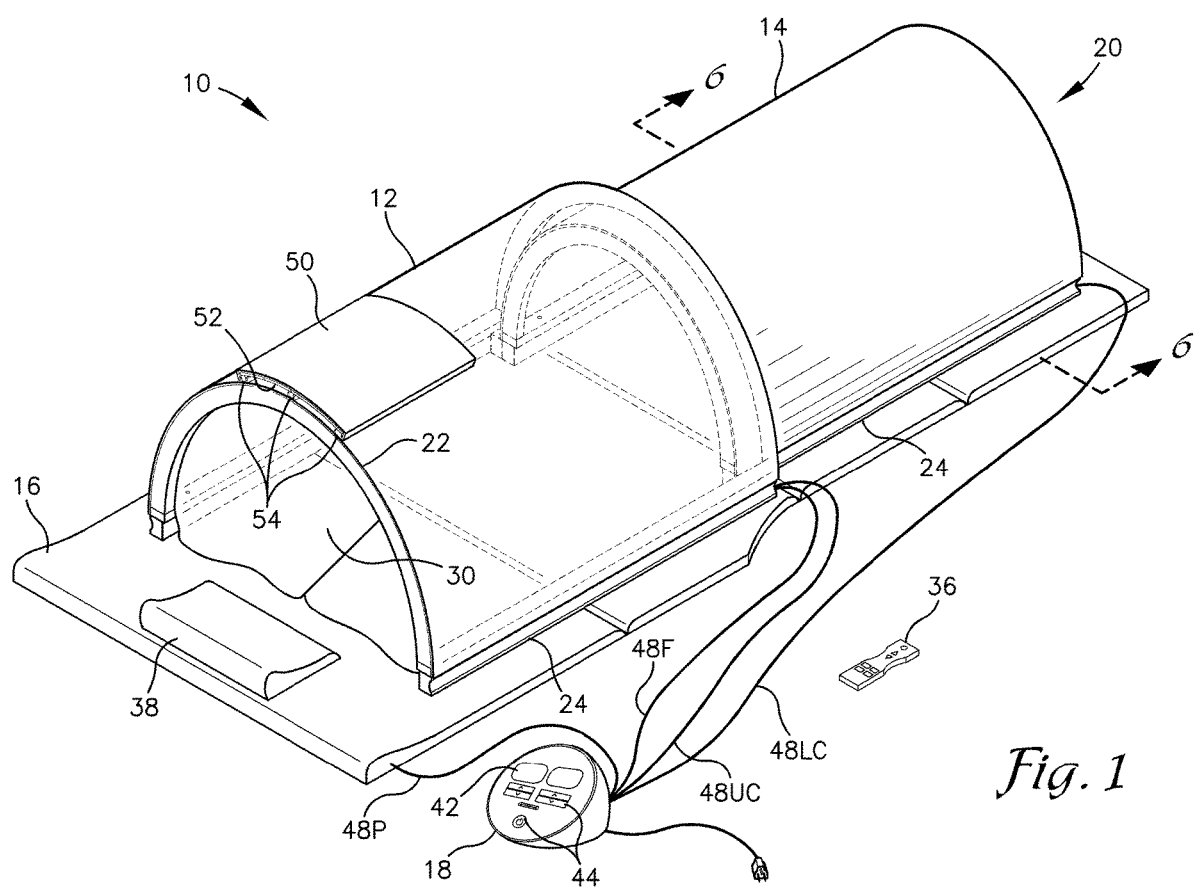
FIG. 1 is a perspective view of a personal therapy chamber with integrated near-infrared radiation emitting elements and a facial treatment fixture depicted in accordance with an exemplary embodiment.

The subject matter of select exemplary embodiments is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described. The terms "about" or "approximately" or "substantially" as used herein denote deviations from the exact value by +/-10%, preferably by +/-5% and/or deviations in the form of changes that are insignificant to the function.

Exemplary embodiments are described herein with respect to the drawings in which reference numerals are employed to identify particular components or features. Similar elements in the various embodiments depicted are provided with reference numerals having matching second and third digits but with differing first digits, e.g. element 10 is similar to elements 110, 210, etc. Such is provided to avoid redundant description of similar features of the elements but is not intended to indicate the features or elements are necessarily the same.

With reference to FIGS. 1 and 4-7, a personal therapy chamber 10 is described in accordance with an exemplary embodiment. The therapy chamber 10 comprises an upper cabin 12, a lower cabin 14, a pad 16, and a control unit 18.

The upper and lower cabins 12, 14 are each configured with a generally half-cylindrical form. The lower cabin 14 has a radial dimension that is slightly smaller than that of the upper cabin 12 such that the lower cabin 14 may be disposed at least partially within the upper cabin 12. The lower cabin 14 also includes an endwall 20 that encloses a distal end thereof. Although the upper and lower cabins 12, 14 are described herein with a half- or semi-cylindrical form, it is understood that other forms can be employed in embodiments of the invention without departing from the scope described herein.

The length of the upper and lower cabins 12, 14 is generally equal and when placed end-to-end is sufficient to enclose the body of a user from the user's shoulders down, e.g. the user's head and at least a portion of the user's neck extend beyond a terminal edge 22 of the upper cabin 12.

The upper and lower cabins 12, 14 may be telescopically moveable relative to one another to adjust the overall length of the therapy chamber 10 and to allow the therapy chamber 10 to be collapsed for storage and/or transportation. The construction of the upper and lower cabins 12, 14 provides a lightweight configuration to aid the movement, storage, and transportation thereof. In one embodiment, the upper and lower cabins 12, 14 are manually moveable by hand by a user without undue strain or strength required of the user.

A rail or guide 24 may be provided along the longitudinal edges of the upper and lower cabins 12, 14 to guide and/or aid relative translational movement of the cabins 12, 14 along a floor surface. The guide 24 may slideably couple the upper and lower cabins 12, 14 along their longitudinal edges. Or the upper and lower cabins 12, 14 may be separate units that can be employed independently. For example, a user may use only one of the upper or lower cabins 12, 14 when a full body therapy treatment is not desired. The user might alternatively employ the upper cabin 12 in an upright, on-end position together with the lower cabin 14 in the lying down position such that the user can sit upright with her torso substantially within the upper cabin 12 and her legs extending beneath the lower cabin 14.

An exterior covering 23 is provided on an exterior surface of the upper and lower cabins 12, 14 and may be at least partially comprised of a fabric formed from carbonized bamboo filament alone or in combination with other fibers, among other fabrics, materials, and textiles.

Figure 5:
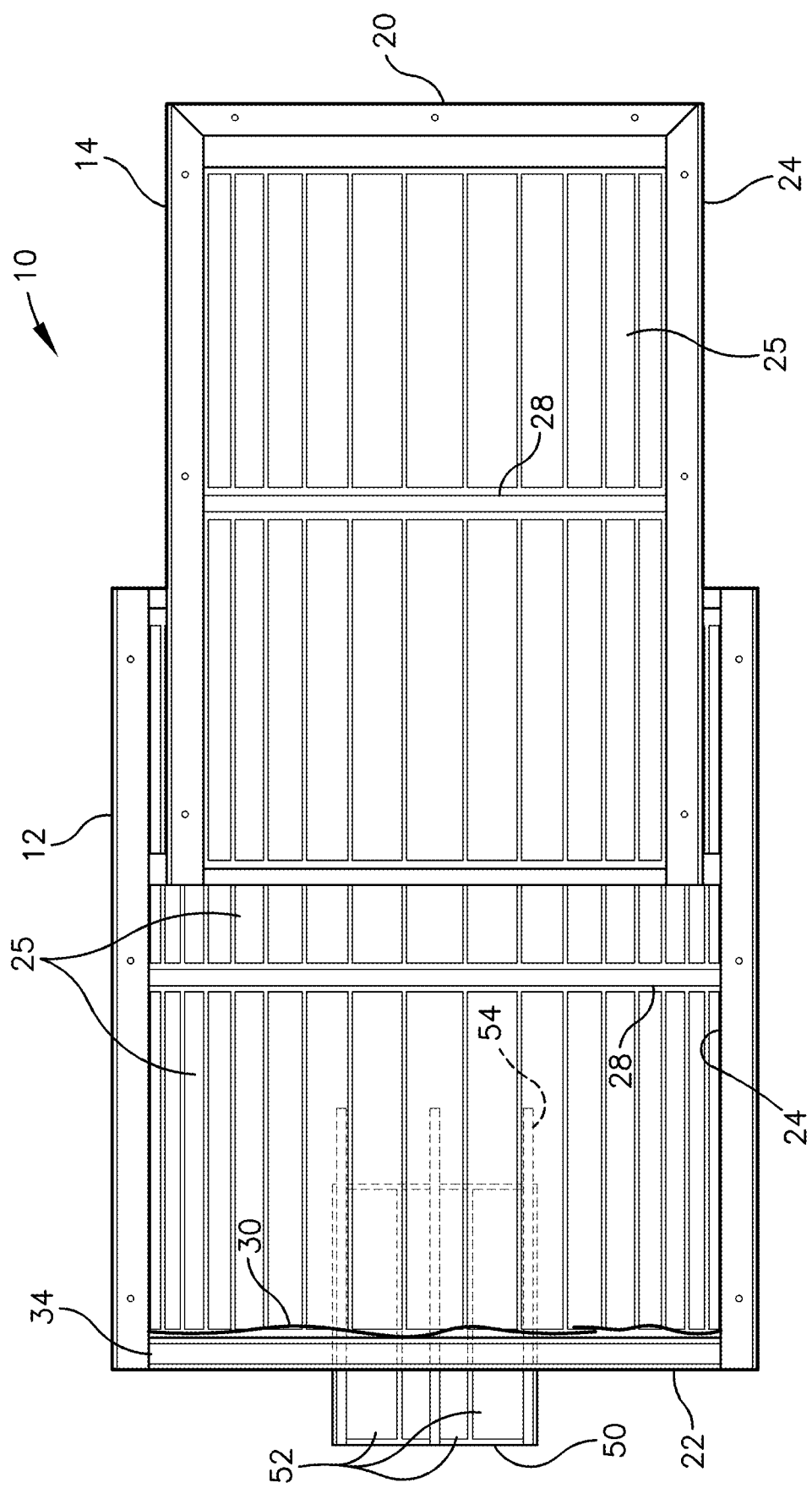
FIG. 5 is a bottom plan view of a cabin of the personal therapy chamber of FIG. 1 showing sections of the cabin and the facial treatment fixture in partially extended states depicted in accordance with an exemplary embodiment.
Figure 6:
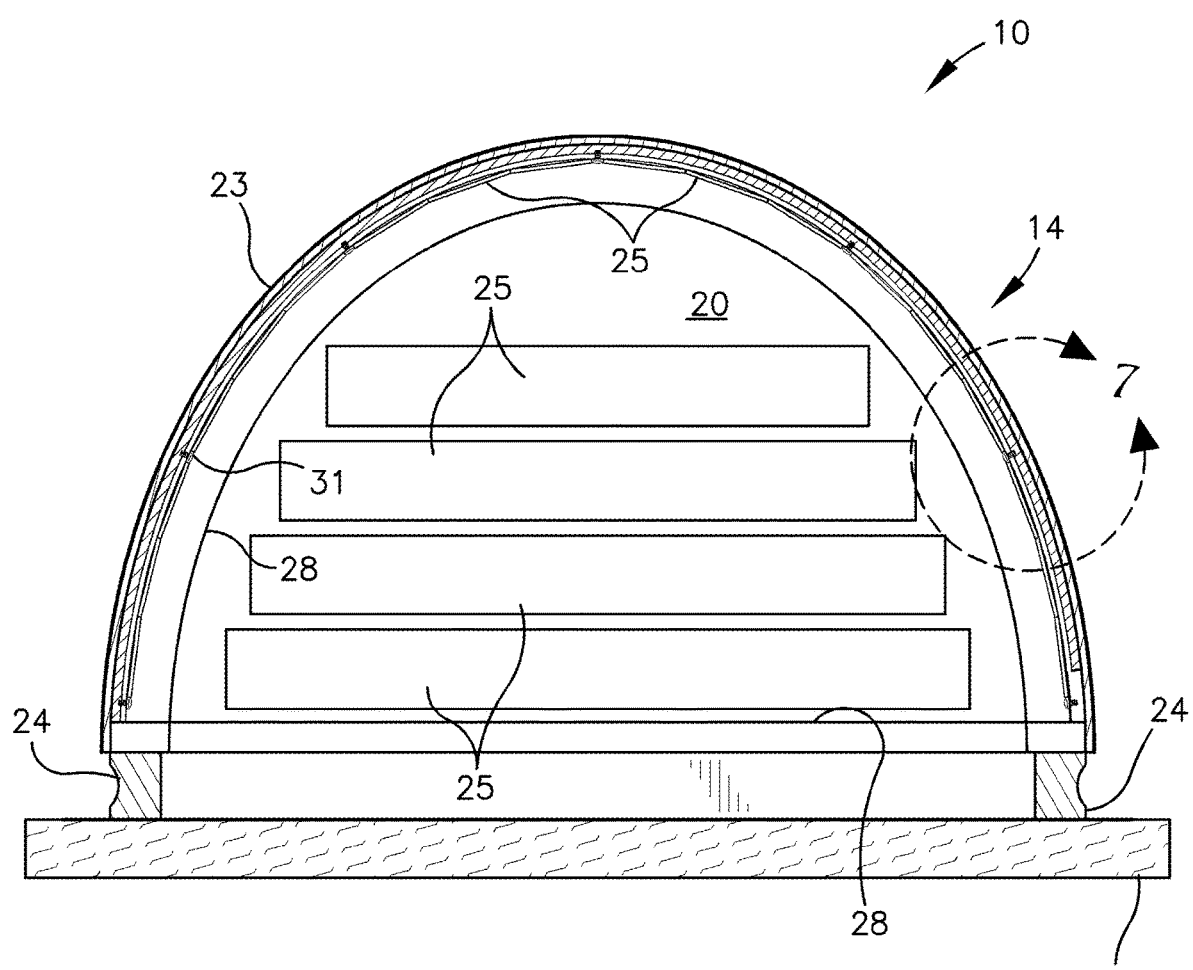
FIG. 6 is a cross-sectional view of the personal therapy chamber of FIG. 1 taken along the line 6-6 of FIG. 1.
Figure 7:
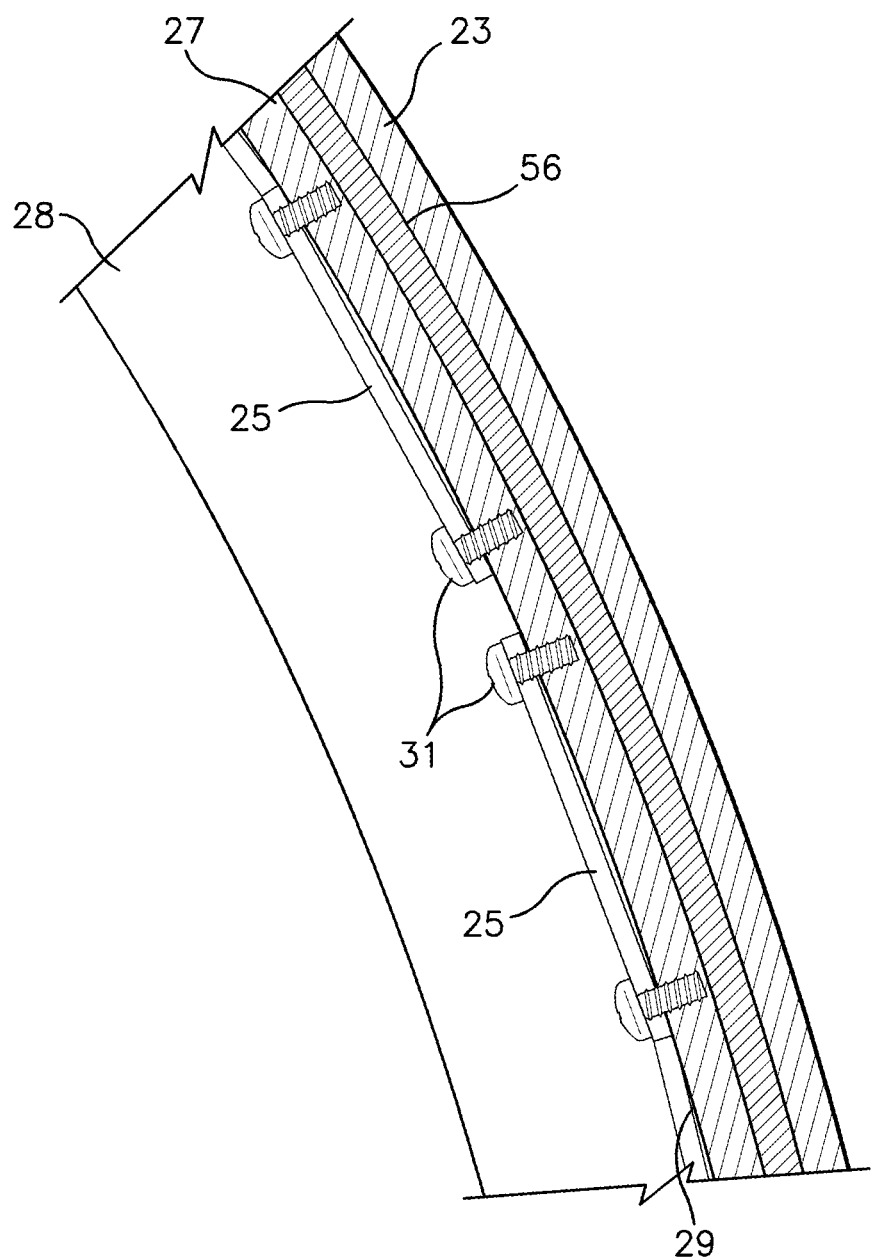
FIG. 7 is an enlarged partial view of a portion of the cross-sectional view of FIG. 6.

As shown in FIG. 5, the upper and lower cabins 12, 14 include a plurality of near-infrared radiation emitting elements 25 disposed on an interior surface of the walls thereof. One or more elements 25 may also be disposed on an interior surface of the endwall 20 of the lower cabin 14. The elements 25 preferably comprise arrays of LEDs (light-emitting diodes) configured to emit near-infrared radiation and which may also emit in the visible light spectrum, e.g. red light. In another embodiment, the elements 25 may comprise or include one or more other forms of heating elements including, for example, flexible planar elements like those described in U.S. Pat. No. 8,737,827 to Zach et al., the disclosure of which is hereby incorporated herein by reference, halogen bulbs, ceramic elements, and the like which emit in the near-infrared spectrum. In another embodiment, the heating elements 25 may comprise or include one or more heating elements including, for example, infrared LEDs, halogen bulbs, ceramic heating elements, and the like, which emit in one or more of the near-, mid- and/or far-infrared radiation spectrums. As such, the user may be simultaneously provided with infrared radiation in one, two, or all three of the near-, mid-, and far-infrared spectrums.

Near-infrared is generally understood as the portion of the infrared spectrum having a wavelength between about 0.5 and about 1.5 micrometers or microns (μm) while mid-infrared is generally understood to comprise wavelengths between about 1.5 and about 7 μm and far-infrared generally comprises wavelengths between about 7 and about 1000 μm although the boundaries of these portions of the spectrum may vary by application.

The elements 25 are preferably configured to produce no or very little electromagnetic field (EMF). In one embodiment, the elements 25 produce EMF that is less than about 3 milliGauss (mG), or more preferably less than about 0.03 mG.

Each of the elements 25 may be independently controllable or may be controlled as a group with one or more other elements 25. Independent control of the elements 25 may enable a user to tailor regions of the user's body that are targeted for application of the infrared radiation therapy.

In one embodiment, the elements 25 are coupled to upper and lower cabins 12, 14 by fasteners 31, adhesives, or the like. The elements 25 may be coupled to frame members 27 extending transversely along an interior of upper and lower cabins 12, 14. In another embodiment, mounting ribs 27 are disposed alongside the frame members 28 of the upper and lower cabins 12, 14. The mounting ribs 27 are disposed along opposing longitudinal faces of the frame members 28 and in abutment therewith and follow the arcuate path of the frame members 28 along the wall of the respective upper or lower cabin 12, 14. In another embodiment, the mounting ribs 27 are integral with the frame members 28.

The mounting ribs 27 provide a mounting surface 29 to which the elements 25 may be coupled. The mounting surface 29 is preferably recessed toward an outer surface of the upper/lower cabin 12, 14 such that, when installed, the elements 25 are recessed radially outward and away from a user positioned in the upper/lower cabin 12,14 or are generally even with an interior surface of the frame members 28. A heat and/or light reflective sheeting or liner 56 can be disposed between the elements 25 and the interior wall of the upper and lower cabins 12, 14.

The upper cabin 12 may include a curtain 30 disposed near the terminal edge 22 thereof. The curtain 30 comprises one or more sections of a flexible material that extend across the distal end of the upper cabin 12 to substantially enclose the opening formed thereby. In one embodiment, the curtain 30 is comprised of a fabric formed from carbonized bamboo filament alone or in combination with other natural and/or synthetic fibers.

As depicted in FIGS. 1 and 5, a facial treatment fixture 50 may be provided near the terminal edge 22 of the upper cabin 12. The facial treatment fixture 50 includes one or more radiation emitting elements 52 configured to emit near-infrared radiation. The elements 52 may also emit visible red light, among other visible, infrared, or other energies. The elements 52 may comprise the same or different emitters as the elements 25 described previously.

The facial treatment fixture 50 is provided on a slideably extendable track 54, arm, or similar mounting apparatus that is coupled to an outer surface of the upper cabin 12 or to the terminal edge 22 thereof. The fixture 50 is thus moveable from a stowed position in which the fixture 50 completely or nearly completely overlies the outer surface of the upper cabin 12 and does not extend beyond the terminal edge 22 thereof as depicted in FIG. 1, to a use position in which the fixture 50 is extended longitudinally beyond the terminal edge 22 and the elements 52 of the fixture 50 do not overlie the upper cabin 12. FIG. 5 depicts the fixture 50 partially extended toward the use position. The fixture 50 and the elements 52 are positioned and dimensioned to overlie a user's face and/or head when in the use position and to direct and emit near-infrared radiation toward the user's face/head.

In the use position, the track 54 or other mounting apparatus may enable the fixture 50 to be adjustably positionable by at least partially pivoting, tilting, rotating, or otherwise moving to adjust the direction in which the infrared energy is directed. The position of the elements 52 may also be adjustable relative to the fixture 50.

Figure 2:
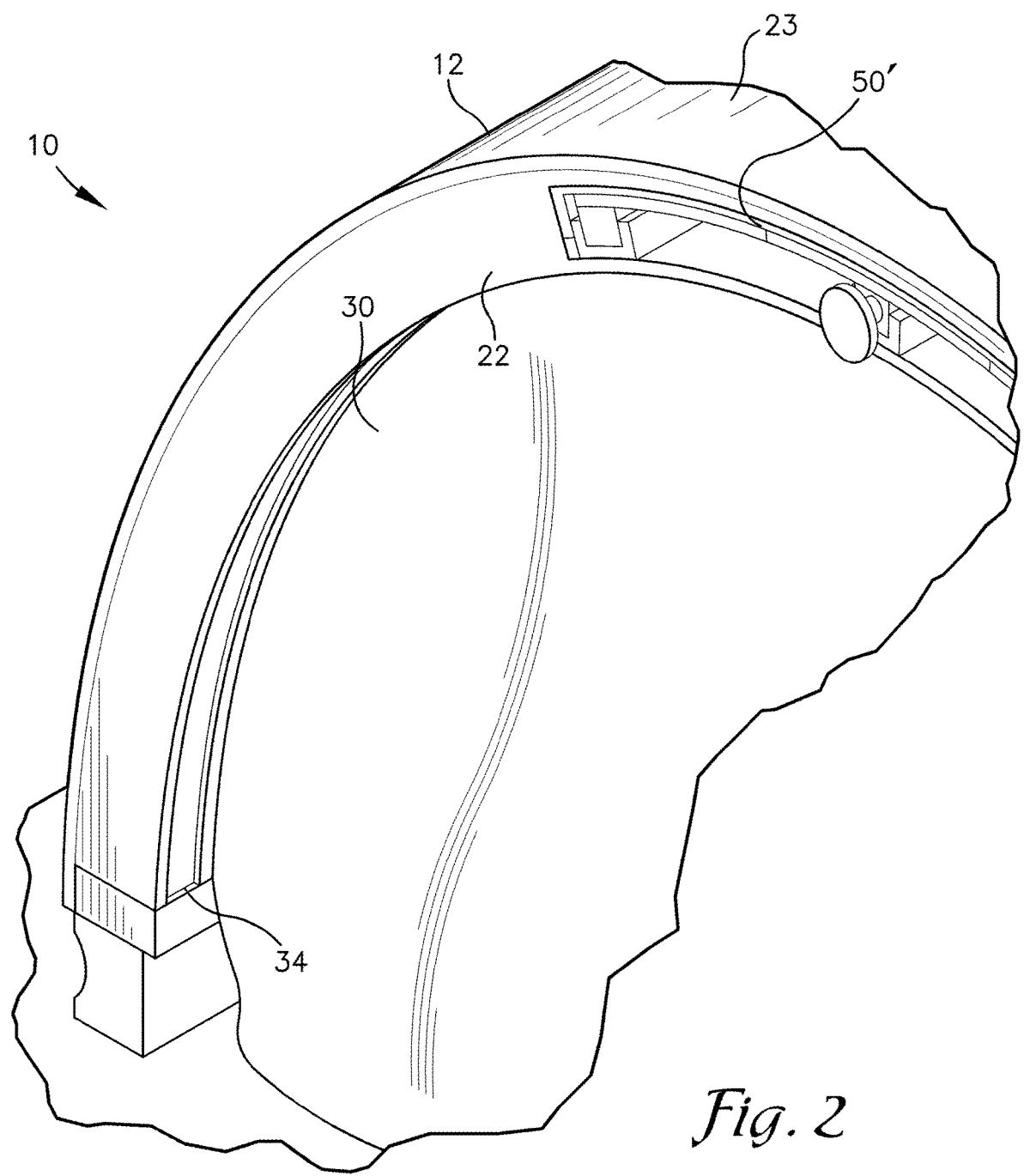
FIG. 2 is a partial enlarged perspective view of a personal therapy chamber with an alternative facial treatment fixture integrated therein in accordance with another exemplary embodiment.
Figure 3:
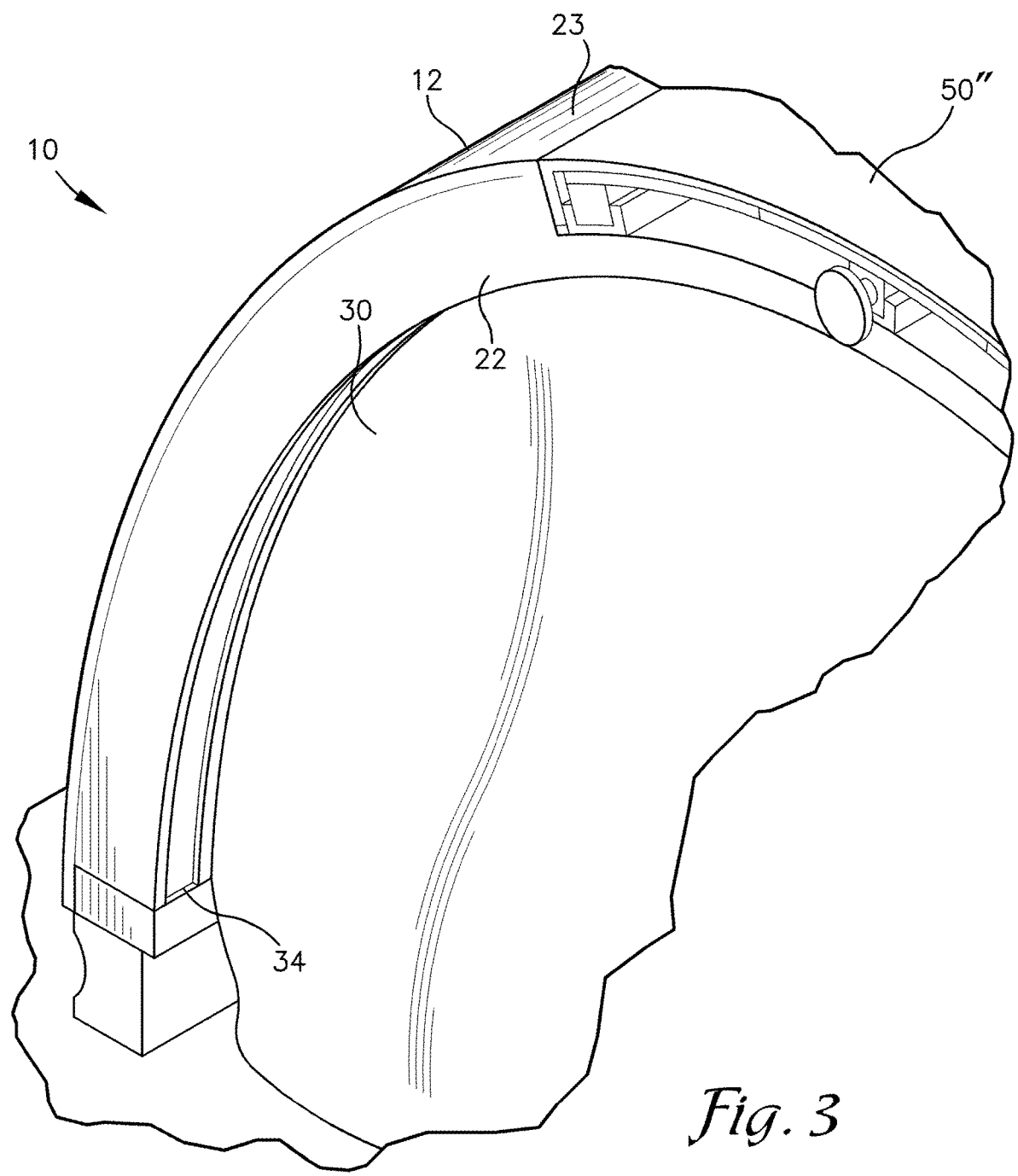
FIG. 3 is a partial enlarged perspective view of a personal therapy chamber with another alternative facial treatment fixture integrated therein in accordance with another exemplary embodiment.

In another embodiment depicted in FIG. 2, the upper cabin 12 includes an opening in the terminal edge 22 and that extends into a space within the thickness of the upper cabin 12 in which the fixture 50' is positioned when in the stowed position. The fixture 50' is thus contained within the thickness of the upper cabin 12 in the stowed position. In another embodiment depicted in FIG. 3, the upper cabin 12 includes a cutout or depression on the outer surface thereof and that extends at least partially into the thickness of the upper cabin 12 and the fixture 50" is sized to fit within the cutout. In the stowed position, the fixture 50" forms a portion of the outer surface of the upper cabin 12.

Figure 4:
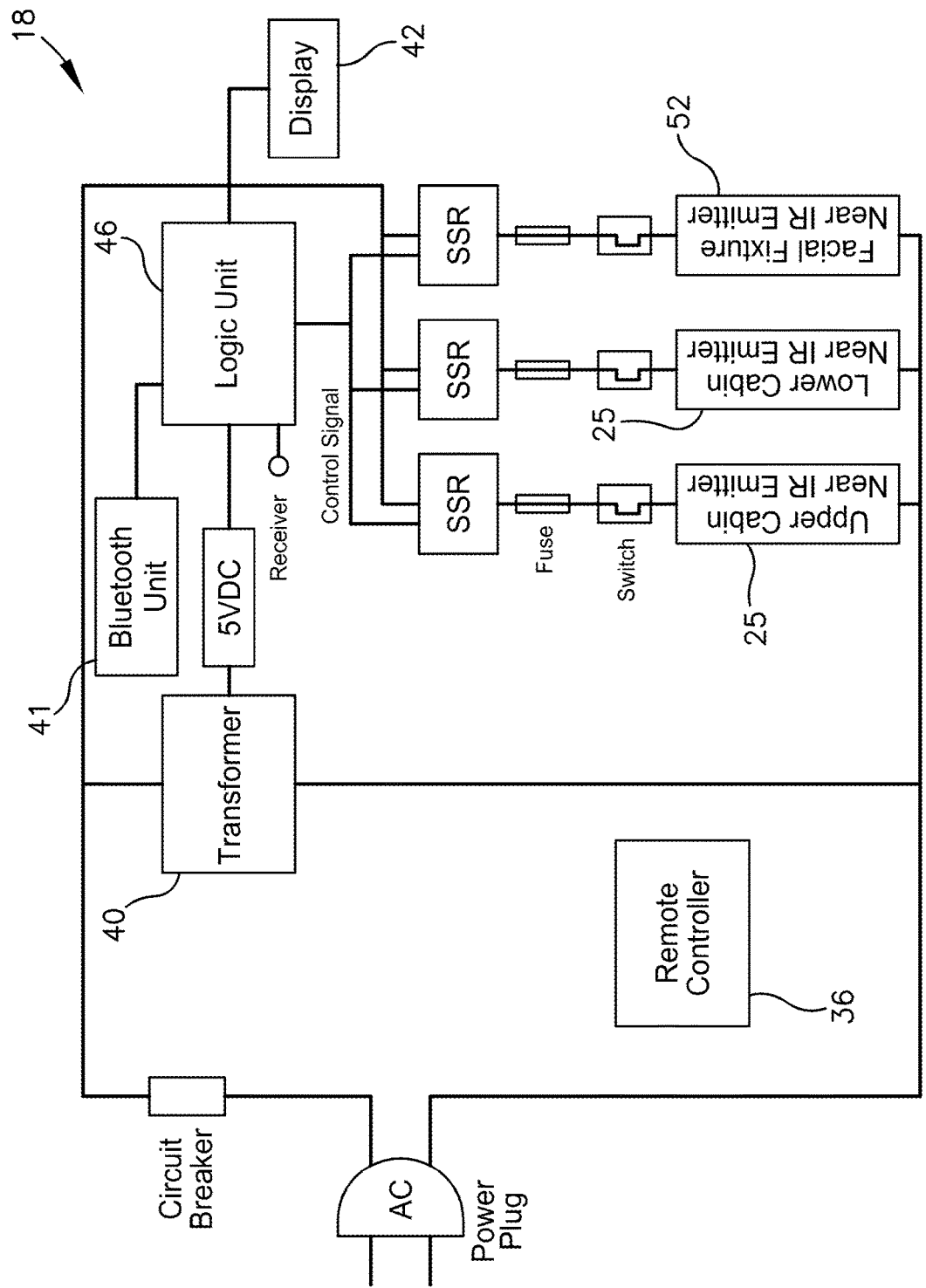
FIG. 4 is a block diagram of a circuit configuration of a control unit for use in the personal therapy chamber of FIG. 1 depicted in accordance with an exemplary embodiment.

As depicted in FIGS. 1 and 4, a wireless or wired remote control unit 36 may be provided to enable the user to turn the elements 25 and 52 on/off and/or to select a desired intensity or other operational characteristic thereof. The remote control 36 can be held in the hand of the user while inside the therapy chamber 10, thus eliminating any need for the user to exit the therapy chamber 10 to operate the fixture 50 or the therapy chamber 10 generally. The remote control 36 may include tactile features that aid the user in identifying buttons and their functions by touch.

The pad 16 comprises a generally planar component formed from a cushioning material, such as a foam, rubber, inflatable bladder(s), or the like. Preferably the pad 16 comprises a memory foam material. The pad 16 may include one or more outer layer materials that enclose the cushioning material, such as a material constructed at least partially from carbonized bamboo fibers. The outer layer materials may provide antimicrobial properties and resistance to sweat or water, among other characteristics.

The pad 16 is divided into a plurality of sections that are foldably joined together to assist folding of the pad 16 for storage or transport. In another embodiment, the pad 16 is a single continuous section that can be rolled upon itself for storage/transport. The pad preferably has a length sufficient to extend the full length of the upper and lower cabins 12, 14 placed end-to-end with the addition of a sufficient length to accommodate the user's head extending from the upper cabin 12. In another embodiment, the user may be provided with a pillow or other pad for accommodating the user's head. The width of the pad 16 can extend beyond the outer perimeter of the upper and lower cabins 12, 14 or can be sized to fit within the perimeter.

The control unit 18 is electrically coupled to the upper cabin 12, the lower cabin 14, the pad 16, and the facial treatment fixture 50 to provide power thereto and to control operations thereof. The control unit 18 receives power from an electrical coupling with a local power grid and distributes the power to each of the components of the therapy chamber 10.

The power grid is typically an alternating current (AC) power source. Referring to FIG. 4, the control unit 18 includes one or more transformers 40 and other components useable to transform AC to direct current (DC) and to provide voltages useable by the elements 25, 52 and the pad 16. Conversion from AC to DC also aids to reduce or eliminate electromagnetic fields produced by the elements 25, 52, 16. Such AC to DC conversions take place within the control unit 18 and/or outside and separated from the upper and lower cabins 12, 14 and the fixture 50 so as to further eliminate or reduce potential exposure of the user to EMF. In another embodiment, AC power is employed directly by the heating elements without conversion to DC.

A wireless communications unit, such as a BLUETOOTH unit 41 may be included in the control unit 18. The BLUETOOTH unit 41 may enable wireless operation/control of the therapy chamber 10 (including the elements 25, 52, among other functions) from a computing device such as a tablet computer, mobile device, smartphone, laptop computer, desktop computer, or the like. The BLUETOOTH unit 41 may employ the wireless communication standards managed by the Bluetooth Special Interest Group, and/or may utilize other wireless communication standards, such as WiFi based on IEEE 802.11 standards, among others.

A clip, clamp, or other mounting device (not shown) may also be provided on the therapy chamber 10 for removeably mounting a computing device on the therapy chamber 10 for use by the user during a therapy session. For example, a tablet computer may be coupled to the therapy chamber 10 along the terminal edge 22 of the upper cabin 12 and held in view of the user such that the user can view video images and/or hear audio output from the tablet computer during the therapy session. The output from the computing device may provide entertainment content to the user and/or information associated with the therapy session or the operation of the therapy chamber 10.

The control unit 18 includes a display 42 and one or more input components 44, such as buttons, switches, dials, or the like as well as one or more logic units 46 that are configured to operate the elements 25, 52, 16 in accordance with inputs provided by the user. The control unit 18 may include a plurality of cords 48 extending therefrom that can be electrically coupled to each of the upper cabin 12 (cord 48UC), the lower cabin 14 (cord 48LC), the pad 16 (cord 48P), and the fixture 50 (cord 48F) to provide electrical communication therebetween. Alternatively, the cords 48 may extend from the upper and lower cabins 12, 14, the pad 16, and the fixture 50 and couple to ports provided on the control unit 18. The cord 48F for the fixture 50 may be integrated into the upper cabin 12 and/or with the cord 48UC for the upper cabin 12 to reduce the number of cords 48 extending from the upper cabin 12 and/or to provide a more aesthetically pleasing appearance.

In operation, a user deploys the pad 16 on a floor surface. The lower cabin 14 and upper cabin 12 may then be placed on the pad 16 with the upper cabin 12 at least partially overlapping the lower cabin 14. The cords 48 are coupled between the pad 16, upper cabin 12, lower cabin 14, and the fixture 50 and the control unit 18. The control unit 18 is coupled to a power grid to receive electrical power therefrom.

The user selects a desired therapy profile, e.g. zones or groups of elements 25, 52, 16, intensity, duration, etc. using the input components 44 and displays 42 provided on the control unit 18. One or more preprogrammed therapy cycles might be provided by the control unit 18 and may be selectable by the user. For example, therapy cycles might be preprogrammed into the control unit 18 by the user or during manufacturing. The control unit 18 might also be configured to provide a dynamic therapy experience in which biological data is collected from the user and employed to select or adjust therapy cycles. For example, the user might wear a heart rate monitor that allows the control unit 18 to adjust a therapy cycle based on the user's heart rate.

The user may enter the therapy chamber 10 by sitting on the pad 16 and inserting her legs into the lower cabin 14. The user might next lie down on the pad 16 and manually telescopically extend the upper cabin 12 from its position overlapping the lower cabin 14 toward her head and over her torso. The upper and lower cabins 12, 14 are lightweight so as to be easily moveable by the user. As a result, the user is enclosed between the pad 16 and the upper and lower cabins 12, 14 with her head and neck extending through the curtain 30 and outside of the upper cabin 12. The user can thus remain enclosed within the therapy chamber 10 for the duration of her desired therapy treatment.

The user can also extend the facial treatment fixture 50 from the terminal edge 22 of the upper cabin 12 to the use position. While within the therapy chamber 10 as described above, the user's head is just outside the upper cabin 12 and near the terminal edge 22 thereof. The fixture 50 is thus positioned to illuminate the user's face with near-infrared and/or visible red light radiation. The user may hold the remote control 36 in a hand while inside the therapy chamber 10 and can thus control the elements 25, 52, 16 without need to move her body (other than for her hand) and without need to exit the upper or lower cabins 12, 14 during the therapy session.

Figure 8:
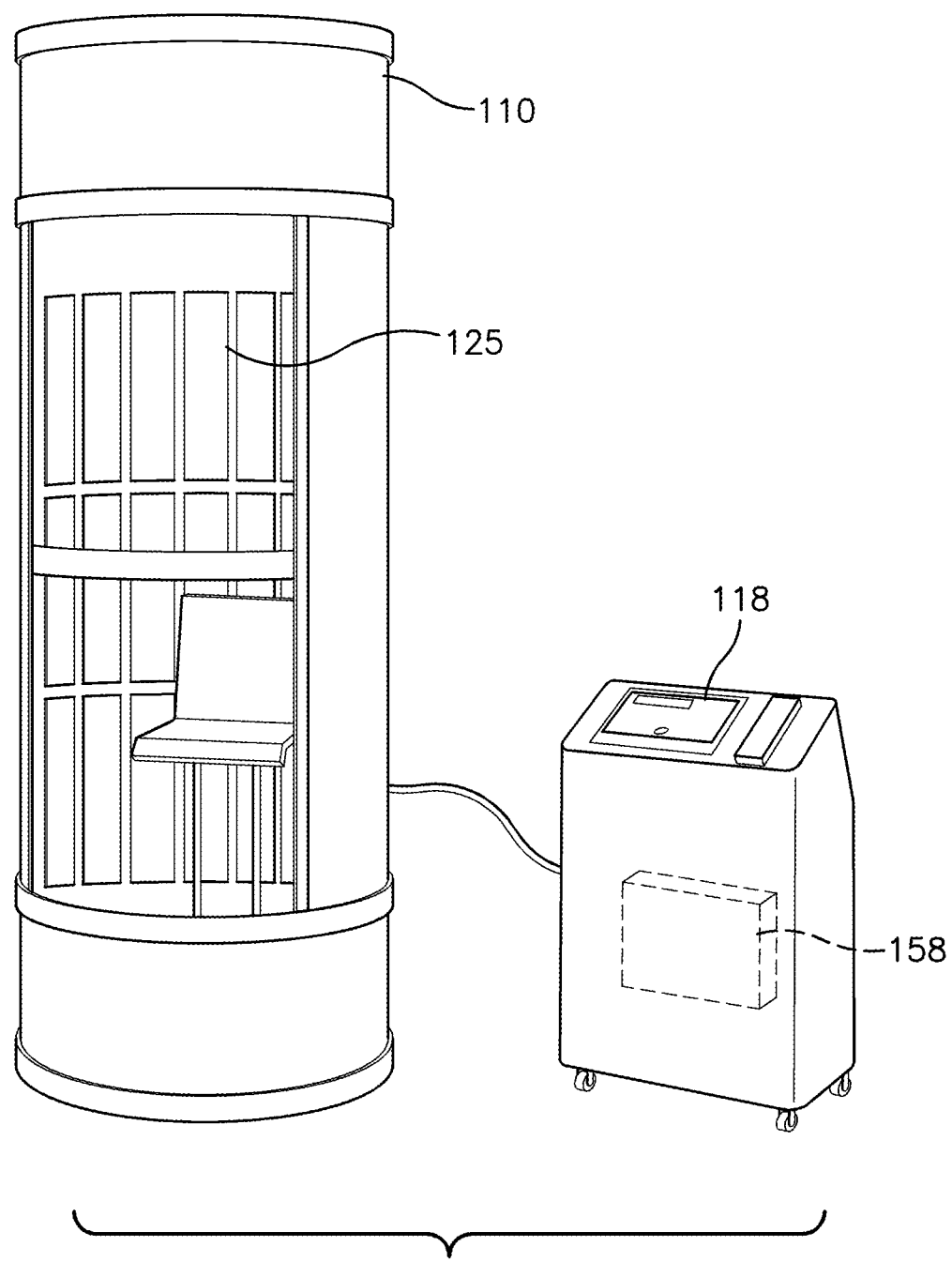
FIG. 8 is a perspective view of another personal therapy chamber configured to provide near-infrared radiation therapy and mild hyperbaric oxygen therapy depicted in accordance with an exemplary embodiment.

With reference now to FIG. 8, in another embodiment, a therapy chamber 110 may be configured to provide both near-infrared radiation treatment and hyperbaric oxygen therapy. The chamber 110 provides a sealable enclosure that may be oriented in a vertical or horizontal position to allow a user to occupy the enclosure in a seated or lying position, respectively. The enclosure includes a plurality of near-infrared radiating elements 125 disposed along interior walls thereof that are positioned and oriented to direct near-infrared radiation toward the user's body.

The chamber 110 is provided with a control unit 118 like the control unit 18 but that is also configured to control operation of a pressurization and oxygenation system 158. The pressurization and oxygenation system 158 is configured to increase the barometric pressure within the chamber 110 up to about 1.2, 1.3, or 1.35 atmospheres or greater. The system 158 may include one or more pumps, compressors, fans, and/or sources of pressurized gas which are employed to increase the barometric pressure within the chamber 110.

The system 158 may operate solely using room air (which may be filtered), or the system 158 may be adapted to include a source of pressurized oxygen (or other gas(es)) that is employed to provide additional oxygen gas into the chamber 110 to increase the oxygen level therein. The system 158 may also mix the oxygen gas with room air to provide a desired gas makeup within the chamber 110. In one embodiment, the system 158 increases a moisture content within the chamber 110, for example by addition of steam or mist to the room air or gasses prior to, or as they are supplied to the chamber 110, among other known methods for increasing the moisture content of the room air and/or gasses. In another embodiment, the chamber 110 is configured to retain and/or be filled by a volume of water in which a user may be positioned to receive infrared radiation, oxygen therapy, and/or hyperbaric treatment while at least being at least partially submerged in the volume of water.

In use, the therapy chamber 110 provides a user with an environment in which the mild hyperbaric oxygen therapy can be received while also receiving near-infrared radiation therapy. Such a configuration may provide additional health and wellness benefits from the combination of treatments that are not seen when the treatments are provided individually. Additionally, combining the treatments decreases the time required for a user to undergo each of the treatments as compared to receiving the treatments individually.

In another embodiment, the therapy chamber 110 is configured like the therapy chamber 10, e.g. with a partial cylindrical form and/or telescoping upper and lower cabins having near-infrared emitting elements therein, with the addition of the pressurization and oxygenation system 158. Such a configuration may incorporate additional sealing elements between the upper and lower cabins and between the cabins and a floor surface or a pad on which they are disposed to aid in maintaining elevated pressures, oxygen levels, and/or moisture levels within the therapy chamber 110. One or both of the upper and lower cabins might also have additional length such that the user's entire body, including their head, may be positioned within the chamber 110. A head wall may be provided to complete and close off the terminal end of the chamber 110. A facial treatment fixture, like the fixture 50, may be formed on an interior wall of the chamber 110 and overlying the user's face when positioned therein.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. A personal therapy chamber comprising:
   a manually portable cabin that is disposable by hand on a surface to define an interior space between a wall of the cabin and the surface in which a single user can be positioned with a head of the user extending at least partially from a terminal end of the cabin;
   a plurality of infrared radiation elements disposed in the wall of the cabin and directed toward the interior space to provide infrared radiation to the user positioned within the cabin, each of the infrared radiation elements comprising an array of LEDs; and
   a facial treatment fixture including a second infrared radiation element disposed to extend from the terminal end of the cabin to be positioned above a face of a user positioned within the cabin, the second infrared radiation element comprising a second array of LEDs.

2. The personal therapy chamber of claim 1, wherein the cabin includes an upper portion and a lower portion that are telescopically movable relative to one another.

3. The personal therapy chamber of claim 1, wherein the facial treatment fixture is moveable between a stowed position in which the fixture is positioned within a space in a thickness of the wall of the cabin and a use position in which the fixture extends longitudinally from the terminal end of the cabin.

4. The personal therapy chamber of claim 1, wherein the facial treatment fixture is moveable between a stowed position in which the fixture is positioned overlying an exterior surface of the wall of the cabin and a use position in which the fixture extends longitudinally from the terminal end of the cabin.

5. The personal therapy chamber of claim 1, wherein the facial treatment fixture is moveable between a stowed position in which the fixture is positioned within a depression in an exterior surface of the wall of the cabin and forms a portion of the exterior surface and a use position in which the fixture extends longitudinally from the terminal end of the cabin.

6. The personal therapy chamber of claim 1, wherein the facial treatment fixture is slideably moveable between a stowed position and a use position.

7. The personal therapy chamber of claim 1, further comprising:
   a wireless remote control configured to be held in hand by the user when positioned in the cabin and useable to control operation of the near-infrared radiation element.

8. The personal therapy chamber of claim 1, further comprising:
   a pressurization system communicably coupled to an interior of the cabin and adapted to increase a barometric pressure within the cabin to a level greater than 1.0 atmosphere.

9. The personal therapy chamber of claim 8, wherein the pressurization system increases an oxygen content within the cabin.

10. The personal therapy chamber of claim 9, wherein the pressurization system increases a moisture content within the cabin.

11. The personal therapy chamber of claim 1, wherein the plurality of infrared radiation elements comprises near-infrared LEDs.

12. A personal therapy chamber comprising:
    a manually portable cabin that is disposable by hand on a surface to define an interior space between an interior wall of the cabin and the surface, the cabin including an upper portion and a lower portion that are telescopically movable relative to one another, the cabin being sized to receive a single user within the interior space with a head of the user extending at least partially beyond a terminal end of the upper portion of the cabin;
    a first infrared radiation element disposed on the interior wall of the cabin and directed toward the space to provide near-infrared radiation to the user positioned within the cabin, the first infrared radiation element comprising a first array of infrared-emitting LEDs; and
    a facial treatment fixture including a second infrared radiation element disposed to extend from a terminal end of the upper portion of the cabin, the second infrared radiation element comprising a second array of infrared-emitting LEDs.

13. The personal therapy chamber of claim 12, wherein the facial treatment fixture is moveable between a stowed position in which the fixture is positioned within a space in a thickness of the wall of the upper portion of the cabin and a use position in which the fixture extends longitudinally from the terminal end of the upper portion of the cabin.

14. The personal therapy chamber of claim 13, wherein the facial treatment fixture is slideably moveable between the stowed position and the use position.

15. The personal therapy chamber of claim 13, wherein the facial treatment fixture is moveable between a stowed position in which the fixture is positioned overlying an exterior surface of the wall of the cabin and a use position in which the fixture extends longitudinally from the terminal end of the cabin.

16. The personal therapy chamber of claim 13, wherein the facial treatment fixture is moveable between a stowed position in which the fixture is positioned within an exterior surface of the wall of the cabin and forms a portion of the exterior surface and a use position in which the fixture extends longitudinally from the terminal end of the cabin.

17. The personal therapy chamber of claim 12, further comprising:
   a pressurization system communicably coupled to an interior of the cabin and adapted to increase one or more of a barometric pressure within the cabin to a level greater than 1.0 atmosphere, an oxygen content within the cabin, and a moisture content within the cabin.

* * * * *